United States Patent [19]

Masuda et al.

[11] Patent Number: 4,950,454

[45] Date of Patent: * Aug. 21, 1990

[54] MEMBER OF ANALYTICAL ELEMENT FOR THE ANALYSIS OF LIQUID SAMPLE CONTAINING SOLID

[75] Inventors: Nobuhito Masuda; Takeshi Igarashi, both of Asaka, Japan

[73] Assignee: Fuji Photo Film Co., Ltd., Kanagawa, Japan

[*] Notice: The portion of the term of this patent subsequent to Aug. 8, 2006 has been disclaimed.

[21] Appl. No.: 338,992

[22] Filed: Apr. 14, 1989

Related U.S. Application Data

[63] Continuation of Ser. No. 98,735, Sep. 16, 1987, Pat. No. 4,855,108, which is a continuation of Ser. No. 728,404, Apr. 29, 1985, abandoned.

[30] Foreign Application Priority Data

Apr. 27, 1984 [JP] Japan .................................. 59-87459
Apr. 27, 1984 [JP] Japan .................................. 59-87460
Apr. 27, 1984 [JP] Japan .................................. 59-87461

[51] Int. Cl.[5] ............................................ G01N 31/22
[52] U.S. Cl. ........................................ 422/56; 422/57; 422/58; 435/805; 436/170; 436/177; 210/500.21; 210/506; 210/927
[58] Field of Search ................................ 422/56–58; 436/170, 177; 210/500.21, 506, 927; 435/805

[56] References Cited

U.S. PATENT DOCUMENTS

| 2,761,791 | 9/1956 | Russell | 264/171 |
| 2,881,072 | 4/1959 | Clark | 162/145 |
| 3,817,379 | 6/1974 | Zipilivan et al. | 210/94 |
| 3,992,158 | 11/1976 | Przybylowicz et al. | 422/57 |
| 4,256,693 | 3/1981 | Kondo et al. | 422/57 X |
| 4,292,272 | 9/1981 | Kitajima et al. | 422/56 X |
| 4,477,575 | 10/1984 | Vogel et al. | 422/56 X |
| 4,551,307 | 11/1985 | Koyama et al. | 422/57 X |

FOREIGN PATENT DOCUMENTS

0045476  2/1982  European Pat. Off. .
0066164  4/1985  Japan .

*Primary Examiner*—Robert J. Warden
*Assistant Examiner*—Jill Johnston
*Attorney, Agent, or Firm*—McAulay Fisher Nissen & Goldberg

[57] ABSTRACT

A member of an analytical element for the analysis of a liquid sample containing solid material, comprising a volume filtration layer composed of a fibrous material and a spreading layer having a liquid-retaining capacity larger than that of the volume filtration layer, in which the volume filtration layer and the spreading layer are united to give an integrated structure. The spreading layer may be composed of a fibrous material, a woven cloth, a knitted cloth or a non-fibrous porous medium.

10 Claims, 2 Drawing Sheets

MEMBER OF ANALYTICAL ELEMENT FOR THE ANALYSIS OF LIQUID SAMPLE CONTAINING SOLID

This is a continuation of application Ser. No. 07/098,735, filed Sept. 16, 1987, now U.S. Pat. No. 4,855,108, which, in turn, is a continuation of application Ser. No. 06/728,404, filed Apr. 29, 1985 now abandoned.

BACKGROUND OF THE INVENTION

1. Field of the invention

The present invention relates to a member of an analytical element which is advantageously employable in the dry system analysis of a liquid sample containing solid material.

2. Description of prior arts

There are known a number of analytical systems for detecting and analyzing biochemical active components present in liquid samples by using a dry analytical element in a layer form (sheet form) (see, U.S. Pat. No. 3,050,373, etc.). Generally, the analysis of the liquid sample in these analytical systems is conducted in such a manner that a reactive component capable of physically or chemically reacting with a substance to be analyzed (an analyte) contained in the liquid sample, is previously incorporated into the analytical element, the reaction of said analyte introduced into the element with said reactive component is allowed to proceed in a biochemical reactive layer and the amount of the reaction product or unreacted component is determined through spectrophotometry or fluorimetry or using isotope radioactivity, thus assaying the analyte.

The above-mentioned dry analytical method has been widely used in the fields of immunological assay utilizing an antigen-antibody reaction or the analysis of enzyme or substrate using an enzyme reaction, since analytical operation is relatively simple. While the analytical method using the analytical element is advantageously simple, there have been made attempts of finding out the layer structure of the analytical element which can give such a wide latitude that the element can be applicable to the analysis of various liquid samples. For example, it has been proposed that in the case of using a liquid containing solid material, particularly whole blood, as a test sample, a blood cell-filtering layer be provided above a reagent layer to filter erythrocyte (i.e., red blood cell). A typical example of such a blood cell-filtering layer is disclosed in Japanese Patent Publication No. 53(1978)-21677 wherein the filtration of blood cells is carried out using a material having a proper porosity. This patent specification teaches that the pore size of the filtering layer should be in the range of 1 to 5 $\mu$m which is smaller than that of the blood cell whose size is in the range of 7 to 30 $\mu$m. Namely, the blood cells can be separated from the liquid phase such as serum and plasma by subjecting the liquid sample to surface filtration in which the blood cells can not penetrate into the filtering layer, but can remain unfiltered on the surface thereof. The blood cell separation by the surface filtration using an analytical element with a built-in blood cell-filtering layer is relatively simple as compared with conventional methods wherein whole blood is subjected to centrifugation. However, the filtering rate is not so high and the filtration layer is liable to be clogged. Consequently, the liquid sample poorly spreads, whereby the analytical sensitivity is lowered with analytical accuracy is reduced.

There is disclosed in Japanese Patent Provisional Publication No. 57(1982)-53661 an element for removing the solid material from blood by separation of plasma and serum by passing it through a layer composed of a specific glass fiber having an average diameter of 0.2 to 5 $\mu$m and a density of 0.1 to 0.5 g./cm$^3$. However, this element is not considered to be fully satisfactory with the blood cell separation ability. According to the description of the examples thereof, the practical separation of plasma (or serum) and blood cell is performed under limitation of the amount of serum or plasma to be applied to a multilayer analytical element in the analytical operation to 50% or less of the absorption amount of the layer and in the presence of a hydrophobic barrier layer. The above separation element has been proposed based on the understanding that serum or plasma passes through the glass fiber at a rate higher than that of blood cell. Thus, the solid-liquid separation on the basis of the volume filtration of the present invention is not suggested.

SUMMARY OF THE INVENTION

An object of the present invention is to eliminate problems associated with conventional analytical methods, such as the complicated operation of previous centrifugal treatment of blood, the clogging of the filtration layer, which is unavoidable in the solid-liquid separation by surface filtration, and insufficient solid-liquid separation ability.

Another object of the invention is to separate solid material from a liquid sample using a filtration method wherein the cubic (three-dimensional) structure of the layer per se is effectively utilized to capture the solid material throughout the volume of the layer (filtration of this type is hereinafter referred to as "volume filtration") in place of conducting the surface filtration described above.

The inventors have made studies on materials and found that specific fibrous materials are effective in separating solid material from a liquid sample containing the solid material by the volume filtration. Further, the inventor has found that when a layer composed of said fibrous material (hereinafter referred to as "volume filtration layer") for capturing solid material is united with a porous liquid sample-spreading layer (hereinafter referred to as "spreading layer") to give an integral structure, a perfect solid-liquid separation can be almost instantaneously achieved.

Accordingly, the present invention provides a member of an analytical element for use in the separation of solid material from a liquid sample containing the solid material, the member comprising a volume filtration layer composed of a fibrous material and a spreading layer wherein the liquid-retaining capacity of the spreading layer is larger than that of the volume filtration layer, and both layers being united to give an integral structure.

The spreading layer can be composed of a fibrous material, a woven or knitted cloth (fabric), or a non-fibrous porous medium.

BRIEF DESCRIPTION OF THE DRAWINGS

FIGS. 1A, 2A, 3A and 4A are illustrated schematically to show the conditions of interface between the volume filtration layer and the spreading layer.

DETAILED DESCRIPTION OF THE INVENTION

The filtration element according to the present invention comprises a volume filtration layer of fibrous material and a spreading layer. The spreading layer is made of material selected from the group consisting of fibrous material, woven cloth, knitted cloth, and non-fibrous porous material (medium).

Figure 1:
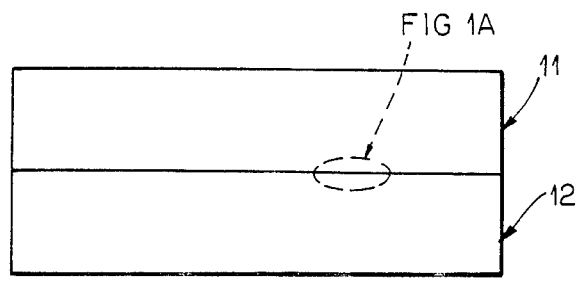
FIGS. 1, 2, 3 and 4 schematically illustrate sectional views of examples of the filtration element comprising the volume filtration layer of fibrous material and the spreading layer, which is employable as member of an analytical element.
Figure 1A:
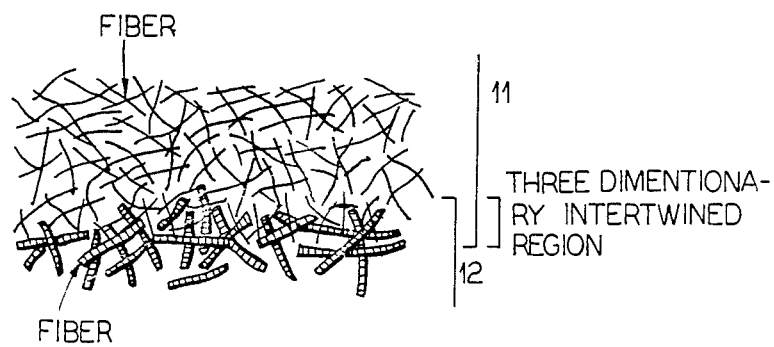
FIGS. 1A, 2A, 3A and 4A are enlarged views of the interface areas which are ovally encircled in FIGS. 1, 2, 3 and 4, respectively.

If the spreading layer is made of fibrous material, the conditions of the interface between the volume filtration layer 11 and the spreading layer 12 are schematically illustrated in FIGS. 1 and 1A, wherein fibers of the volume filtration layer 11 are three-dimensionally intertwined with fibers of the spreading layer 12.

Figure 2:
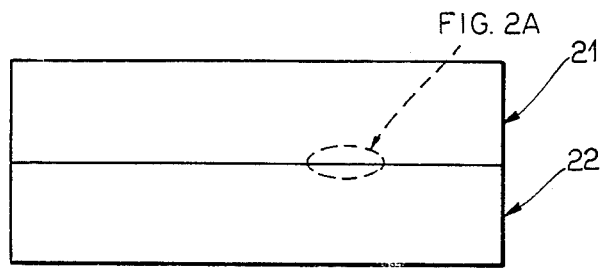
Figure 2A:
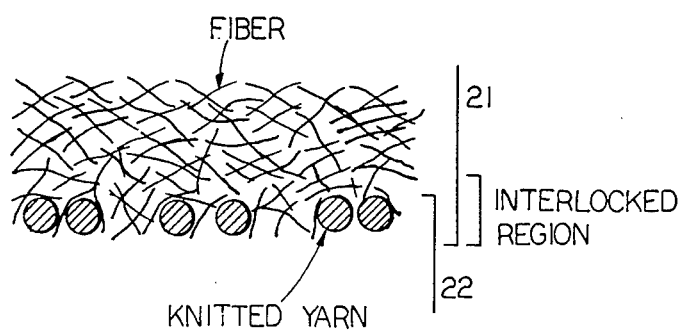

If the spreading layer is made of knitted cloth, the conditions of the interface between the volume filtration layer 21 and the spreading layer 22 are schematically illustrated in FIGS. 2 and 2A, wherein fibers of the volume filtration layer 21 are interlocked with the spreading layer 22.

Figure 3:
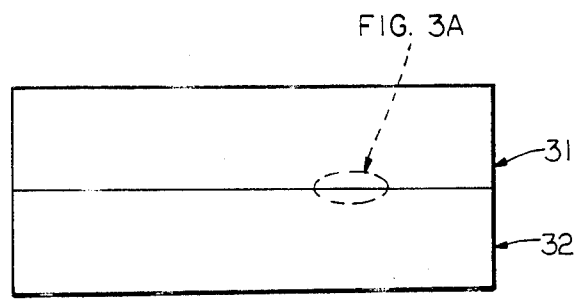
Figure 3A:
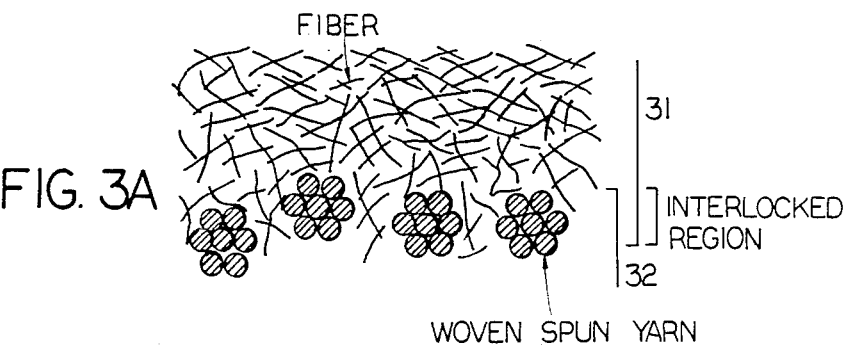

When the spreading layer is made of woven cloth, the conditions of the interface between the volume filtration layer 31 and the spreading layer 22 are schematically illustrated in FIGS. 3 and 3A, wherein fibers of the volume filtration layer 31 are interlocked with the spreading layer 32.

Figure 4:
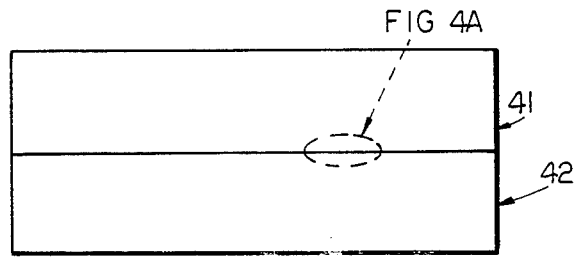
Figure 4A:
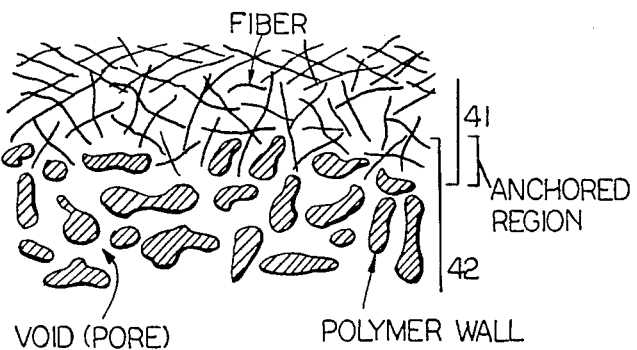

When the spreading layer is made of non-fibrous porous material, such as, a blushed polymer, the conditions of the interface between the volume filtration layer 41 and the spreading layer 42 are schematically illustrated in FIG. 4 and 4A, wherein fibers of the volume filtration layer 41 are anchored to micropores (voids) of the spreading layer 42.

Examples of the fibrous material which is employable for the preparation of the volume filtration layer of the invention include inorganic fibers such as glass fiber and asbestos; natural organic fibers such as cotton, flax, pulp and silk; and semisynthetic and synthetic fibers such as viscose rayon, cuprous ammonical rayon, cellulose acetate, partially formalized polyvinyl alcohol, polyethylene, polypropylene, polyvinyl chloride, polystyrene and polyesters (e.g. polyethylene terephthalate). Among them, glass fiber is preferred. The fibrous materials should be substantially inert to the liquid sample or analyte.

Preferably, the fibrous material constituting the volume filtration layer of the invention has a density of about 0.02 to 0.1 g./cm$^3$, a diameter of about 0.1 to 5 $\mu$m and a length of about 100 to 4,000 $\mu$m. The fibrous material can be obtained, for example, by classifying the materials to from 10 to 200 Tyler mesh size in a conventional manner. The fibrous material for the formation of the filtration layer is controlled so that the material has a liquid-retaining capacity smaller than that of the material of the spreading layer such as a fibrous material, a woven or knitted cloth, or a non-fibrous porous material.

The liquid retaining capacity is defined substantially by the denseness of air gaps of the layer (voids), the clearance of the layer space, the diameter of the fibrous material, etc. If the material of either one is decided, the other material can be chosen so as to meet the above requirements.

For example, when a filter paper (e.g., GC-50, manufactured by Toyo Filter Paper Co., Ltd.) very densely formed from a relatively fine glass fiber having a short fiber length is used as the spreading layer, the volume filtration layer can be easily formed by applying a slurry containing fibers dispersed therein to the surface of said filter paper by a paper-making method, under the conditions that said fiber is the same as that for the spreading layer or has a larger diameter or a longer length than that for the spreading layer. More particularly, a material of the spreading layer is first chosen, and a relatively dense spreading layer is formed. A material for the filtration layer is then chosen and a bulky volume filtration layer having a lower density than that of the spreading layer is superposed on the spreading layer to give the integral structure by a paper-making process. The above method is a simple one.

In the case that the fibrous material is employed for the formation of the spreading layer, the finer and the shorter fiber is employed, the more dense spreading layer can be formed. From the viewpoint of the paper-making process, the denseness of the resulting spreading layer increases with increase of pressure difference or the specific gravity of the slurry. A calendering under pressure after the application of the production of paper-like layer is an effective method for preparing a dense spreading layer. With regard to the volume filtration layer, the material and the preparing method are contrarily chosen, and this layer is combined together with the spreading layer in an integral form.

In the case that the spreading layer is made of a woven cloth such as broad cloth or a knitted cloth such as tricot cloth, a material for the volume filtration layer having a similar, thicker and/or longer fiber is chosen and a bulky volume filtration layer having a lower density than that of the cloth is superposed on the cloth (i.e., spreading layer) to give the integral structure by a paper-making process.

In the case that the spreading layer is made of a non-fibrous porous material such as membrane filter, a material for the volume filtration layer having a thick and/or long fiber is chosen, and a bulky volume filtration layer having a lower density than that of the non-fibrous porous spreading layer is superposed on the latter layer to give the integral structure by a paper-making process. In this case, it should be noted that the fibrous material for the filtration layer is selected to contain short fibers. The short fibers stick into the pores of the porous spreading layer, whereby the volume filtration layer is anchored to the spreading layer.

As described hereinbefore, the spreading layer can be composed of fibrous material, a woven or knitted cloth or a non-fibrous porous medium.

In the first place, the spreading layer composed of fibrous material is described.

As the fibrous material for the spreading layer used in the present invention, there can be used conventional fibrous materials having a metering function capable of uniformly spreading the liquid sample. Examples of such fibrous materials are those having a density of 0.1 to 2.0 g./cm$^3$. Typical examples of such fibrous materials include natural fibers such as wood (cellulose) pulp, cotton, silk and wool; semisynthetic fibers such as cellulose esters and viscose rayon; synthetic fibers such as polyamide, polyester (e.g. polyethylene terephthalate and polyolefin; inorganic fibers such as glass fiber and asbestos; and fibrous materials obtained by untying filter paper. These fibrous materials for the spreading layer may be subjected to a treatment for making them hydrophilic. Such treatment, fibrous materials and the formation of the spreading layer are disclosed in more detail in Japanese Patent Provisional Publications No. 55(1980)-164356 and No. 57(1982)-66359, etc.

The liquid-retaining capacity varies depending on various factors, and one of them is a void ratio. It is difficult to give a strict range of the liquid-retaining capacity of the volume filtration layer and the spreading layer. However, it is generally advantageous that void ratio for the volume filtration layer is adjusted to at least about 85%, preferably at least 95%, and the void ratio for the spreading layer is adjusted to about 50 to 90%.

In one aspect, the member of an analytical element of the present invention is characterized in that the volume filtration layer composed of the above fibrous material and the spreading layer composed of the above fibrous material are combined together in an integral form. The term "integral form" or "integral structure" used herein is different from the conventional integral form (or integral structure, which is obtained by simply laminating a plurality of layers and placing the resulting laminate under pressure or combining them together by means of a binder or an bonding material) in that the integral form (or integral structure) of the invention is in the form of a random structure where the fibrous materials of the volume filtration layer and the spreading layer are three-dimensionally intertwined (or interlocked) with one another on the interface between both layers. This three-dimensional random structure is not chemically formed, but physically formed and firmly integrated so that this interfacial structure is hardly broken and they can no longer be divided into the original two layers without deformation.

The member for the solid-liquid separation according to the present invention can be prepared in the following manner.

(1)

(a) A fibrous material for the volume filtration layer is untied into pieces. If necessary, the length is controlled by means of a screen clasifier.

(b) The fibrous material obtained in the above stage (a) is dispersed in a liquid dispersion medium such as water or a mixture of water and an organic solvent miscible with water to prepare a slurry (i.e., a stuff solution). By choosing a proper dispersion medium or adding a water-soluble solute such as sucrose, there can be obtained a slurry having the desired specific gravity and viscosity. The selection of the dispersion medium and the material to be added can be made by a known density gradient method. In the preparation of the slurry, there may be optionally added additives such as a dispersant, a viscosity modifier, an antiseptic agent and the like which are conventionally used in the paper-making process. Any of conventional slurry-preparing methods may be used without specific limitation. For example, there may be used a method using a conventional mixing apparatus such as a magnetic stirrer, an agitating spring, a homogenizer or a ball mill and a method using a beater in the preparation of the slurry.

(2) A fibrous material for the spreading layer is untied into pieces, and if necessary, the length is adjusted in a similar manner to that described in the (1)-(a). The resulting fibrous material in the untied form is subjected to the slurry-preparing operation in a similar manner to that described in the (1)-(b).

(3) Confirmation is made on that the slurries obtained in the above procedures (1) and (2) are not mixed with each other on the interface therebetween. In order to form the slurries which are not mixed with each other, they are generally so prepared that a certain difference in specific gravity can be introduced therebetween. For this purpose, a known density-gradient method can be utilized. Such immiscible slurries can be prepared by utilizing a difference in specific gravity as well as viscosity. For example, a difference in viscosity is introduced by adding a water-soluble polymer such as synthetic polymer, gum or polysaccharide serving as a thickner.

While the above descriptions have been directed to conditions for wetted cases, i.e., the slurry, it will be understood that when one of them is under a dry condition they are not mixed with each other. Thus, it is not always necessary to adopt the above-described conditions.

(4) The two kinds of the slurries prepared under the above-described conditions such that they are immiscible, are placed in a container and processed according to a known paper-making process. In more detail, the slurry having a higher specific gravity (and/or higher viscosity) forms the lower layer, while the slurry having a lower specific gravity (and/or lower viscosity) forms the upper layer. These slurries are filtered on a filter (e.g. wire cloth, cylindrical wire cloth, paper-making wire or membrane filter) by means of suction to remove the dispersion medium. During the application of the paper-making procedure, the fibers in the slurries are intertwined (or interlocked) with one another at the interface between both layers, whereby forming the desired three-dimensional random structure.

(5) The thickness of the resulting product in layers is set using a member having a given clearance therebetween. For example, said layer-form product is interposed between two sheets of said member and compressed. Alternatively, the layer-form product is passed between rollers having a given slit. These methods are described in more detail in Japanese Patent Application No. 57(1982)-211382. In this way, the thickness of the layer-form product is set to a range of preferably 100 to 2,000 $\mu$m, and the product is dried without causing a change in the thickness.

For this purpose, it is preferred to conduct the drying procedure at a relatively low temperature, and freeze-drying is particularly preferred. The drying procedure may be carried out before the setting of the thickness.

In the second place, the spreading layer composed of a woven or knitted cloth is described.

Examples of the woven cloth (woven fabric) which can be used for the spreading layer include those disclosed in Japanese Patent Provisional Publication No. 55(1980)-164356 and No. 57(1982)-66359. Among the woven cloth, plain weave fabrics made of warp and weft are preferred. Among plain woven fabrics, thin cloth, muslin, broadcloth and poplin are preferred.

Examples of yarns for woven cloth include those composed of the same materials as those constituting knitted cloths as described in more detail hereinafter. Any of filament yarn and spun yarn (twist yarn) can be used, and the spun yarn is preferred. The yarn diameter of the woven cloth is generally in the range of about 20S to about 150S, preferably about 40S to about 120S in terms of cotton spinning yarn count or in the range of about 35 to about 300D, preferably about 45 to about 130D in terms of silk thread denier. The thickness of the woven cloth is generally in the range of about 100 to about 500 μm, preferably about 120 to 350 μm. The voids (void ratio) of the woven cloth are generally in the range of about 40 to about 90%, preferably about 50 to about 85%.

Examples of the knitted cloth which can be used as the spreading layer include many kinds of knitted cloths, among which warp knitted fabric and weft knitted fabric are preferred. Examples of the warp knitted fabrics include single atlas knitted cloth, tricot knitted cloth, double tricot knitted cloth, milanese knitted cloth and rashar knitted cloth. Examples of the weft knitted fabrics include plain weave knitted cloth, pearl knitted cloth, rubber knitted cloth, and double face knitted cloth. Examples of the yarns for knitted fabrics include yarns of natural fibers such as cotton, silk and wool; yarns composed of fine fibers or single fibers of regenerated cellulose (e.g. viscose rayon and cupra), semisynthetic organic polymer (e.g. cellulose diacetate and cellulose triacetate), synthetic organic polymer (e.g. polyamide such as nylon, acetalated polyvinyl alcohol such as vinylon, polyacrylonitrile, polyethylene terephthalate, polyethylene, polypropylene and polyurethane), and yarns composed of fiber blends of a natural fiber and a regenerated cellulose or a semisynthetic or synthetic organic polymer fiber. Any of filament yarn and spun yarn can be used, and spun yarn is preferred. The diameter of the yarn for knitted fabric is generally in the range of from about 40 to 150S, preferably about 60 to about 120S in terms of cotton spinning yarn count, or in the range of about 35 to about 130D, preferably about 45 to about 90D in terms of silk thread denier. The number of knitting gauge of the knitted fabric is generally in the range of about 20 to about 50. The thickness of the knitted fabric is generally in the range of about 100 to about 600 μm, preferably about 150 to about 400 μm. The voids of the knitted fabric are generally in the range of about 40 to about 90%, preferably about 50 to about 85%. The warp knitted fabric, tricot knitted cloth, rashar knitted cloth, milanese knitted cloth and double tricot knitted cloth are preferred, because shrinkage in the wale's direction is small, the operation in the lamination stage of knitted goods is easy and the stitches are not easily loosened during cutting.

As mentioned hereinbefore, the liquid-retaining capacity varies depending on various factors, and one of them is the void ratio. It is difficult to give a strict range of the liquid-retaining capacity of the volume filtration layer and the spreading layer. However, it is generally advantageous that void ratio for the volume filtration layer are at least about 85%, preferably at least 95%, and the void ratio for the spreading layer are about 50 to 90%.

The member of an analytical element of the present invention is characterized in that the volume filtration layer composed of the above fibrous material and the spreading layer composed of the woven or knitted cloth are combined together in an integral form in the same manner as described for the spreading layer of a fibrous material.

The member for the solid-liquid separation can be prepared in the following manner.

(1) The slurry for the formation of the volume filtration layer is prepared in the same manner as in the aforementioned stage (1).

(2) The slurry was slowly placed on a woven or knitted cloth and filtered on a filter (e.g. wire cloth, cylinderical wire cloth, paper-making wire or membrane filter) by means of suction to remove the dispersion medium. During the application of the paper-making process, the fibers in the slurry are intertwined (or interlocked) with fibrous matrix of the woven or knitted cloth on the interface between both layers, whereby forming the desired three-dimensional random structure. Thus formed composite is then processed in the same manner as described with respect to the formation of the volume filtration layer on the spreading layer of a fibrous material.

In the third place, the spreading material of a non-fibrous porous material is described.

There are known a variety of non-fibrous porous materials showing so-called "metering function". Examples of the non-fibrous porous material include a blushed polymer prepared from such a polymer as polycarbonate, polyamide, cellulose ester, or the like. As appropriate blushed polymers, there can be mentioned Microfilter (tradename, Fuji Photo Film Co., Ltd.), Millipore (tradename, Millipore Corp.), Metricel (tradename, German Instrument Inc.). Details of the non-fibrous porous material are described in Japanese Patent Provisional Publication No. 49(1974)-53888, U.S. Pat. No., 3,992,158, etc.

The composite member comprising the volume filtering layer and the non-fibrous porous spreading layer in an integral form can be prepared in the same manner as in the preparation of the member using the spreading layer of a woven or knitted cloth.

The member of the present invention can be used to form a multilayer analytical element comprising one or a plurality of layers (e.g. a reaction layer, a reagent layer, a light-blocking layer, etc.) laminated on one another and is arranged in such a manner that the volume filtration layer forms the outermost layer on which a liquid sample is spotted (deposited).

When a liquid sample containing solid material is spotted on the member of the invention provided to an analytical element, the solid material is captured in the volume filtration layer. The capturing is made throughout the volume filtration layer as the liquid sample passes therethrough, so that the separation of the solid material from the liquid phase can be effected without causing clogging.

It is thought that the liquid-retaining capacity of the spreading layer cooperates with the volume filtration to accomplish more efficiently the separation of the solid material from the liquid phase in a short time. The uniform, rapid spreading of the liquid is accelerated under the above-described interfacial conditions.

In performing the analysis, a multilayer analytical element provided with the member of the invention is used in the following manner. A given amount of a solid-containing liquid sample which contains an analyte is deposited dropwise on the volume filtration layer of the member of the invention, said volume filtration layer being positioned as the uppermost layer of the multilayer analytical element. The solid-liquid separation is carried out in the member of the invention and only the liquid phase penetrates into a reaction layer, a reagent layer, etc. to effect a corresponding biochemical reaction. A signal corresponding to the amount of the analyte generates and is measured by a known method.

The following examples will further illustrate the present invention in more detail, but in no way to be construed as limiting the present invention.

EXAMPLE 1

Preparation of spreading layer composed of glass fiber filter paper and provided with volume filtration layer (1) Preparation of glass fiber dispersion 2 g. of glass fiber filter paper GA-100 (manufactured by Toyo Filter Paper Co., Ltd.) was cut into 2 mm square pieces. To this was added 800 ml of water, and the pieces were dispersed therein using an Ace homogenizer AM-11 (manufactured by Nippon Seiki Seisakusho Co., Ltd.). The dispersion was screened through a Tyler mesh No. 12 sieve to remove a lump of glass fiber. Thus, a glass fiber dispersion was obtained. The amount of the glass fiber solid in the dispersion was measured according to the manner that 10 ml of the dispersion was filtered through a filter (manufactured by Millipore Corporation provided with a membrane filter (diameter: 47 mm, pore size: 0.22 μm, Microfilter manufactured by Fuji Photo Film Co., Ltd.)), the resulting solid together with the filter was dried and weighed, and the weight of the filter previously weighed was deducted. The amount of the glass fiber solid in the dispersion was 22 mg./10 ml.

(2) Preparation of spreading layer provided with volume filtration layer

A 55 mm-diameter glass fiber filter paper GC-50 (manufactured by Toyo Filter Paper Co., Ltd.) was fixed to a filter device of 47 mm-diameter type (manufactured by Millipore Corporation). 15 ml (solid content: 33 mg.) of the slurry prepared in the above (1) was mixed with 100 ml of water, and the aqueous mixture was filtered on the filter by a paper-making procedure. After filtration was complete, the resulting product was placed between two sheets of Teflon-coated glass sheets with a spacer which was thicker than the thickness of GC-50 by 500 μm. After an excess of water was squeezed out, the product was frozen on a dry ice. After removal of the glass sheets, freeze-drying was conducted. Thus, a spreading layer provided with a volume filtration layer [member (A)] was prepared.

(3) Comparison of blood (whole blood)-spreading ability

For the purpose of examining the ability of the filtration layer prepared in the above (2), fresh blood containing an anticoagulant was deposited dropwise on each of the member (A) and a simple glass fiber filter paper (GC-50). After the lapse of exactly five minutes, the diameter of a circle spread over the volume filtration layer or the glass fiber filter paper (GC-50) was measured. 10 Experiments were conducted for each sample. The mean value ($\bar{x}$) of the diameter and the standard deviation ($\sigma$) were calculated. The results are set forth in Table 1 (unit: mm).

TABLE 1

| Amount of blood deposited | 10 μl | 20 μl |
|---|---|---|
| Member (A) of Present invention | 6.1 ± 0.16 | 8.6 ± 0.21 |
| Simple glass fiber (Filter paper GC-50) | 4.9 ± 0.32 | 5.5 ± 0.29 |
| | | ($\bar{x} \pm \sigma$ mm) |

When blood was deposited on the simple glass fiber filter paper, blood remained on the surface thereof even after the lapse of five minutes and blood cells were spread over the whole surface thereof. On the other hand, when blood was deposited on the member (A) of the invention, it was observed that blood cells were captured in the volume filtration filter after about one minute and only plasma was spread.

EXAMPLE 2

Preparation of spreading layer composed of filter paper and provided with volume filtration layer (1) Preparation of spreading layer provided with volume filtration layer.

A glass fiber dispersion (solid content: 15 mg./10 ml) was obtained in the same manner as that described in Example 1-(1).

Filter No. 5C (manufactured by Toyo Filter Paper Co., Ltd.) was sticked on a filter device of 47 mm-diameter type (manufactured by Millipore Corporation) with water. A mixture consisting of 15 ml (solid content: 22.5 mg.) of the above glass fiber dispersion and 50 ml of water was filtered on the filter by a paper-making procedure.

After the filtration was complete, the product was placed between two glass sheets with a spacer of 650 μm, the thickness of the product was made to a given size, and the product was frozen on dry ice. After removal of the glass sheets, freeze-drying was conducted to prepare a spreading layer provided with a volume filtration layer (member B).

(2) Evaluation of blood-spreading ability

For the purpose of examining the ability of the volume filtration layer composed of the glass fiber, each of 10, 20 and 30 μl of blood containing an anticoagulant was deposited on each of the member B and the simple filter paper (No. 5C), and the spreadability within the filter paper was examined. 10 Experiments were conducted for each sample. The mean value ($\bar{x}$) of the diameter of the spread circle and the standard deviation ($\sigma$) were calculated. The results are set forth in Table 2.

TABLE 2

| Amount of deposited blood | 10 μl | 20 μl | 30 μl |
|---|---|---|---|
| Member (B) of Present invention | 6.9 ± 0.13 | 8.6 ± 0.19 | 11.9 ± 0.23 |
| Simple filter (No. 5C) | 5.4 ± 0.12 | 6.8 ± 0.25 | 7.9 ± 0.31 |

($\bar{x} \pm \sigma$ mm)

When blood was deposited on the simple filter paper, blood remained on the surface thereof and blood cells were spread over the whole surface thereof as in Example 1-(3). On the other hand, when blood was deposited on the member B of the invention, only plasma was well-spread rapidly without causing the spreading of blood cells.

EXAMPLE 3

Preparation of spreading layer composed of cotton-polyester mixed spun yarn cloth and provided with volume filtration layer

(1) Preparation of spreading layer provided with volume filtration layer

A 55 mm-diameter cotton-polyester mixed spun broad cloth (cotton 35%/65% polyethylene terephthalate, spun yarn of 80S, thickness of the cloth: approx. 150 $\mu$m) was fixed to a 55 mm-diameter membrane filter (Microfilter manufactured by Fuji Photo Film Co., Ltd.). 15 ml (solid content: 33 mg.) of the slurry prepared in the same manner as in Example 1-(1) was mixed with 100 ml of water, and the aqueous mixture was filtered on the filter device by a paper-making procedure. After filtration was complete, the resulting product was placed between two Teflon-coated glass sheets with a spacer which was thicker than the thickness of the cloth by 500 $\mu$m. After an excess of water was squeezed out, the product was frozen on a dry ice. After removal of the glass sheets, freeze-drying was conducted. Thus, a spreading layer provided with a volume filtration layer [member (C)] was prepared.

(2) Comparison of blood (whole blood)-spreading ability

For the purpose of examining the ability of the filtration layer prepared in the above (1), fresh blood containing an anticoagulant was deposited dropwise on each of the member (C) and a simple broad cloth (the same as above, cotton 35/65 polyester). After the lapse of exactly five minutes, the diameter of a circle spread over the glass fiber filter paper (GC-50) or the broad cloth was measured. 10 Experiments were conducted for each sample. The mean value ($\bar{x}$) of the diameter and the standard deviation ($\sigma$) were calculated. The results are set forth in Table 3 (unit: mm).

TABLE 3

| Amount of blood deposited | 6 $\mu$l | 10 $\mu$l |
|---|---|---|
| Member (C) of Present invention | 7.8 ± 0.19 | 10.1 ± 0.21 |
| Simple broad cloth (cotton-polyester) | 11.5 ± 0.31 | 14.7 ± 0.35 |
| | | ($\bar{x}$ ± $\sigma$ mm) |

When blood was deposited on the simple broad cloth, blood remained on the surface thereof even after the lapse of five minutes and blood cells were spread over the whole surface thereof. On the other hand, when blood was deposited on the member (C) of the invention, it was observed that blood cells were captured in the volume filtration filter after about one minute and only plasma was spread.

EXAMPLE 4

Preparation of cotton spreading layer provided with volume filtration layer

(1) Preparation of a spreading layer provided with volume filtration layer.

A glass fiber dispersion was obtained in the same manner as in Example 1-(1).

A cotton broad cloth (100% spun yarn, of 80S, thickness of cloth: approx. 150 $\mu$m) was sticked on a filter device in the same manner as in Example 3-(1). Then, the same procedure was repeated to prepare a cotton spreading layer provided with a volume filtration layer (member D).

(2) Evaluation of blood-spreading ability

The procedure of Example 3-(2) was repeated to compare the blood-spreading ability between the member D and the simple cotton cloth. The results are set forth in Table 4.

TABLE 4

| Amount of blood deposited | 6 $\mu$l | 10 $\mu$l |
|---|---|---|
| Member (D) of Present invention | 6.2 ± 0.32 | 8.1 ± 0.40 |
| Simple broad cloth (cotton) | 9.5 ± 0.41 | 12.3 ± 0.49 |
| | | ($\bar{x}$ ± $\sigma$ mm) |

When blood was deposited on the simple cotton cloth, blood cell was separated on the periphery of the spread circle. On the other hand, when blood was deposited on the member D of the invention, only plasma was well-spread rapidly into the cotton spreading layer without causing the spreading of blood cells.

EXAMPLE 5

Preparation of polyester spreading layer provided with volume filtration layer

(1) Preparation of spreading layer provided with volume filtration layer.

A glass fiber dispersion was obtained in the same manner as in Example 1-(1).

A polyester broad cloth (100% spun yarn, of 80S, thickness of cloth: approx. 150 $\mu$m) was sticked on a filter device in the same manner as in Example 3-(1). Then, the same procedure was repeated to prepare a polyester spreading layer provided with a volume filtration layer (member E).

(2) Evaluation of blood-spreading ability

The procedure of Example 3-(2) was repeated to compare the blood-spreading ability between the member E and the simple polyester broad cloth. The results are satisfactory on the member E.

EXAMPLE 6

Preparation of spreading layer composed of microfilter and provided with volume filtration layer

(1) Preparation of glass fiber dispersion 2 g. of glass fiber filter paper GA-100 (manufactured by Toyo Filter Paper Co., Ltd. was cut into 2 mm square pieces. This was placed in a agate mortar and beaten in the presence of water to loosen the matrix. To this was added 800 ml of water, and the fibers were dispersed therein using an Ace homogenizer AM-11 (manufactured by Nippon Seiki Seisakusho Co., Ltd.). The dispersion was screened through a Tyler mesh No. 12 sieve to remove a lump of glass fiber. Thus, a glass fiber dispersion was obtained. The amount of the glass fiber solid in the dispersion was measured according to the manner that 10 ml of the dispersion was filtered through a filter device (manufactured by Millipore Corporation provided with a membrane filter (diameter: 47 mm, pore size: 0.22 $\mu$m, Microfilter manufactured by Fuji Photo Film Co., Ltd.)), the resulting solid together with the filter was dried and weighed and the weight of the filter previously weighed was deducted. The amount of the glass fiber solid in the dispersion was 23 mg./10 ml.

(2) Preparation of spreading layer provided with volume filtration layer

A Microfilter FM-80 (tradename, Fuji Photo Film Co., Ltd., pore size: 0.8 μm) was fixed to a filter device (for the 47 mm-type use, Millipore Corporation.) 10 ml of the slurry prepared in the above (1) was mixed with 100 ml of water, and the aqueous mixture was filtered on the filter by a paper-making procedure. After filtration was complete, the resulting product was placed between two Teflon-coated glass sheets with 350 μm clearance. After an excess of water was squeezed out, the product was frozen on a dry ice. After removal of the glass sheets, freeze-drying was conducted. Thus, a microfilter spreading layer provided with a volume filtration layer [member (F)] was prepared.

(3) Comparison of blood (whole blood)-spreading ability

For the purpose of examining the ability of the filtration layer prepared in the above (2), fresh blood containing an anticoagulant was deposited dropwise on each of the member (F) and a simple microfilter (the same FM-80). After the lapse of exactly five minutes, the diameter of a circle spread over the volume filtration layer or the microfilter was measured. 10 Experiments were conducted for each sample. The mean value ($\bar{x}$) of the diameter and the standard deviation (94) were calculated. The results are set forth in Table 5 (unit: mm).

TABLE 5

| Amount of deposited blood | 10 μl | 20 μl | 30 μl |
|---|---|---|---|
| Member (F) of Present invention | 7.8 ± 0.09 | 10.8 ± 0.13 | 13.4 ± 0.20 |
| Microfilter FM-80 | 3.5 ± 0.11 | 5.2 ± 0.11 | 6.5 ± 0.18 |

($\bar{x} \pm \sigma$ mm)

When blood was deposited on the simple microfilter, a small portion of the blood was absorbed in the microfilter, while most of the blood remained on the surface thereof even after the lapse of five minutes. Further, blood cells were spread over the whole surface thereof. On the other hand, when blood was deposited on the member (F) of the invention, it was observed that blood cells were captured in the volume filtration filter after about one minute and only plasma was spread.

EXAMPLE 7

The procedure of Example 6 was repeated except that the volume filtration layer was prepared independently and pressed on the microfilter, to prepare a member. In this member, however, the transfer of the liquid sample from the filtration layer to the microfilter took place irregularly and the results fluctuated.

The results given hereinabove indicate that by incorporating the member of the present invention into the multilayer analytical element, the liquid sample containing solids can be rapidly analyzed with high accuracy. Such liquid sample containing solids has to be heretofore treated with a specifically prepared means, since an error is brought about in analysis. When the member of the invention is used, the solid material is captured in the volume filtration layer so that the liquid phase is spread over the spreading layer having a high liquid-retaining capacity in a very short time without causing clogging.

The member of the present invention is particularly effective in the analysis of liquid samples such as whole blood, turbid urine, body fluids and chyle serum. For example, when the member of the present invention is used for the analysis of whole blood samples having different solid contents (whole blood samples having different hematocrit values), plasma is quantitatively supplied to the spreading layer, irrespective of whether the hematocrit value varies, so that plasma spreads over an area corresponding to the quantity of plasma by the metering function of the spreading layer. In other words, in the case that the member of the present invention is used for the analysis of whole blood, analysis can be made without being influenced by fluctuation in hematocrit value and without causing an error in analysis.

We claim:

1. A filtration element for use in the analysis of a liquid sample containing solid material which comprises a volume filtration layer and a spreading layer having a liquid retaining capacity larger than that of the volume filtration layer, wherein the volume filtration layer is made of fibrous material having a diameter of 0.1 to 1.0 μm and a length of 10–4,000 μm and has a density of 0.02 to 0.1 g/cm$^3$, the spreading layer is made of fibrous material, the volume filtration layer and the spreading layer are united to give an integrated structure to have an interface between both layers, and the fibrous material of the volume filtration layer and the fibrous material of the spreading layer are three-dimensionally intertwined with one another at the interface.

2. The filtration element as claimed in claim 1 wherein said spreading layer has a density of 0.1 to 2.0 g/cm$^3$.

3. The filtration element as claimed in claim 2 wherein the fibrous material of the spreading layer has a diameter of 0.1 to 1.0 μm and a length of 10–4,000 μm.

4. The filtration element as claimed in claim 1 wherein the volume filtration layer has a void ratio of at least about 85 percent.

5. The filtration element as claimed in claim 4 wherein the void ratio is at least 95 percent.

6. The filtration element as claimed in claim 4 wherein the spreading layer has a void ratio of from about 50 to 90 percent.

7. The filtration element as claimed in claim 1 wherein the volume filtration layer has a void ratio of at least 95 percent and the spreading layer has a void ratio of from about 50 to 90 percent.

8. The filtration element as claimed in claim 1 wherein the spreading layer is composed of glass fiber.

9. The filtration element as claimed in claim 1 wherein the volume filtration layer is composed of glass fiber.

10. The filtration element as claimed in claim 1 wherein the spreading layer and volume filtration layer are composed of glass fiber.

* * * * *